(12) United States Patent
White et al.

(10) Patent No.: US 6,585,770 B1
(45) Date of Patent: Jul. 1, 2003

(54) DEVICES FOR SUPPORTING BONY STRUCTURES

(75) Inventors: John L. White, Bartlett, TN (US); Eddie F. Ray, III, Cordova, TN (US); John Stewart Young, Memphis, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 264 days.

(21) Appl. No.: 09/692,530

(22) Filed: Oct. 19, 2000

(51) Int. Cl.$^7$ .................................................. A61F 2/44
(52) U.S. Cl. .................................................. 623/17.11
(58) Field of Search .......................... 623/16.11, 17.11, 623/17.15, 17.16; 606/61, 86

(56) References Cited

U.S. PATENT DOCUMENTS

| | | |
|---|---|---|
| 3,710,789 A | 1/1973 | Ersek |
| 4,820,305 A | 4/1989 | Harms et al. |
| 5,015,247 A | 5/1991 | Michelson |
| 5,055,104 A | 10/1991 | Ray |
| 5,458,638 A | 10/1995 | Kuslich et al. |
| 5,489,308 A | 2/1996 | Kuslich et al. |
| 5,571,192 A | 11/1996 | Schonhoffer |
| 5,591,235 A | 1/1997 | Kuslich |
| 5,593,409 A | 1/1997 | Michelson |
| 5,609,635 A | 3/1997 | Michelson |
| 5,658,285 A | 8/1997 | Marnay et al. |
| 5,683,394 A | 11/1997 | Rinner |
| 5,702,451 A | 12/1997 | Biedermann et al. |
| 5,723,013 A | 3/1998 | Jeanson et al. |
| 5,725,580 A * | 3/1998 | Cloutier et al. ................ 623/16 |
| 5,741,253 A | 4/1998 | Michelson |
| 5,776,197 A | 7/1998 | Rabbe et al. |
| 5,785,710 A | 7/1998 | Michelson |
| 5,885,299 A | 3/1999 | Winslow et al. |
| 5,897,556 A | 4/1999 | Drewry et al. |
| 6,086,613 A | 7/2000 | Camino et al. |
| 2001/0014826 A1 * | 8/2001 | Biedermann et al. ..... 623/17.11 |
| 2002/0099443 A1 * | 7/2002 | Messerli et al. .......... 623/17.11 |

FOREIGN PATENT DOCUMENTS

| | | |
|---|---|---|
| EP | 0 369 603 | 5/1990 |
| WO | WO 99/56675 | 11/1999 |

OTHER PUBLICATIONS

Pyramesh Titanium Mesh Brochure, Sofamor Danek, Sofamor Danek USA, 1997.

* cited by examiner

Primary Examiner—Todd E. Manahan
(74) Attorney, Agent, or Firm—Woodard, Emhardt, Moriarity, McNett & Henry LLP

(57) ABSTRACT

A device for supporting weak bony structures includes a body having first and second ends configured for contacting adjacent bony structures. The body has a wall that with a number of opening, and the wall defines a hollow chamber for receiving bone growth inducing material. The device includes an end cap for placement in the hollow chamber adjacent one of the ends of the body. The end cap has opposite upper and lower surfaces, and includes a plurality of arms extending from a central ring. Each of the arms having a first end connected with the ring and an opposite second end including an outer surface. Each of the outer surfaces are positionable adjacent the inner surface of the wall of the body when the end cap is inserted into the hollow chamber. Each arm can also include a projection that extends at least partially into a wall opening.

72 Claims, 3 Drawing Sheets

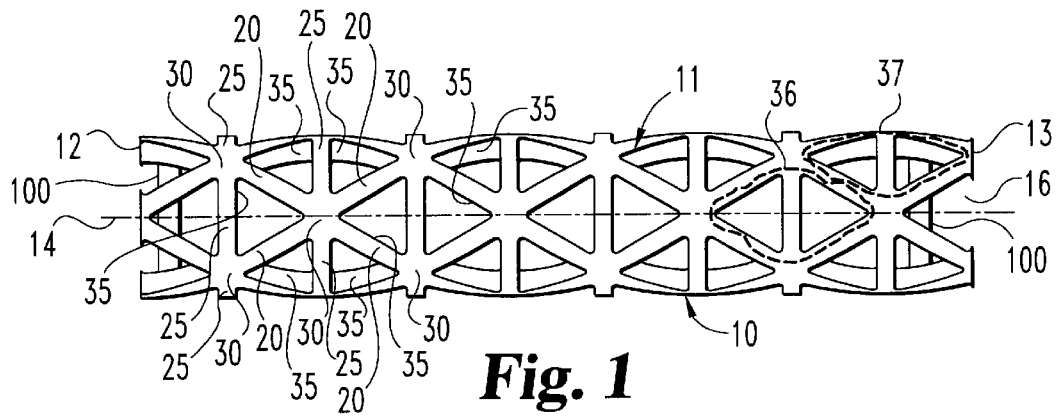
Fig. 1
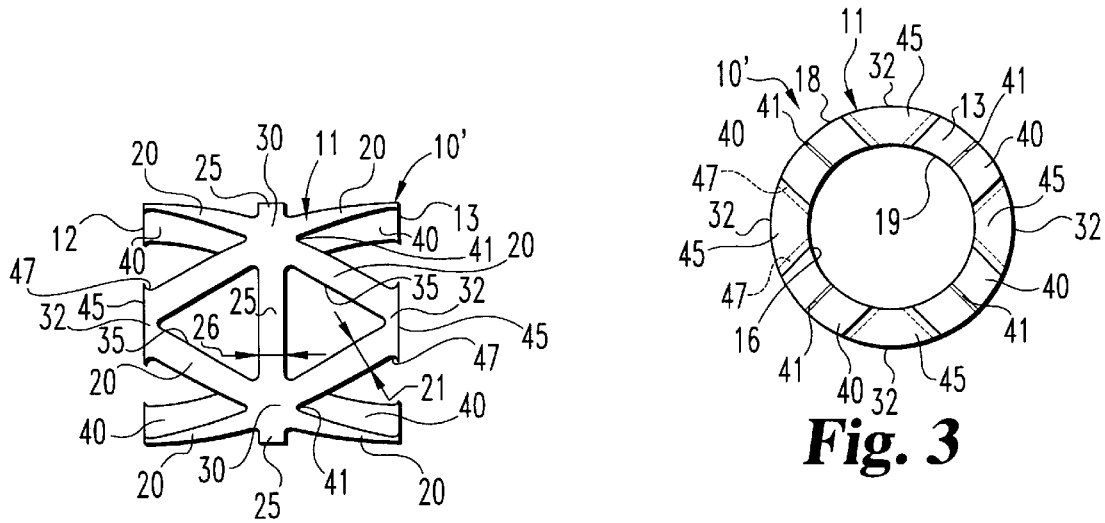
Fig. 2
Fig. 3
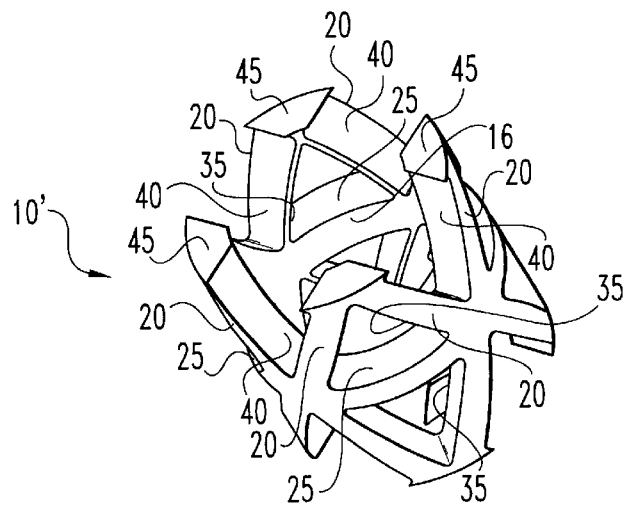
Fig. 4

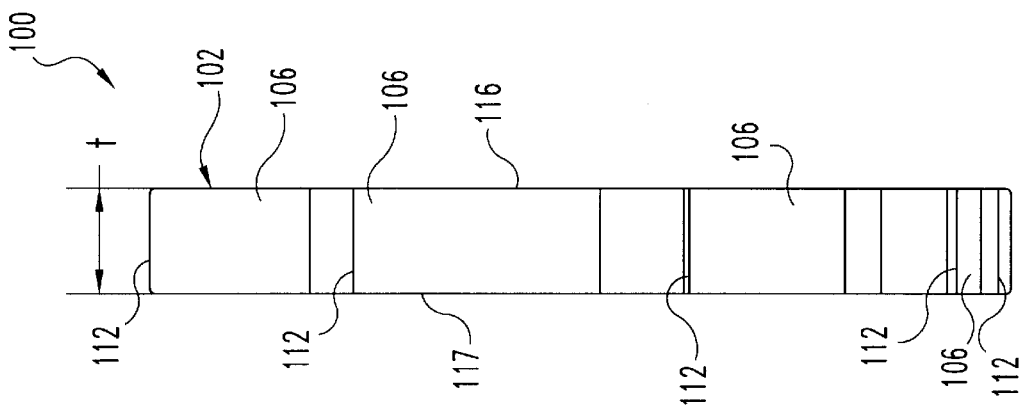
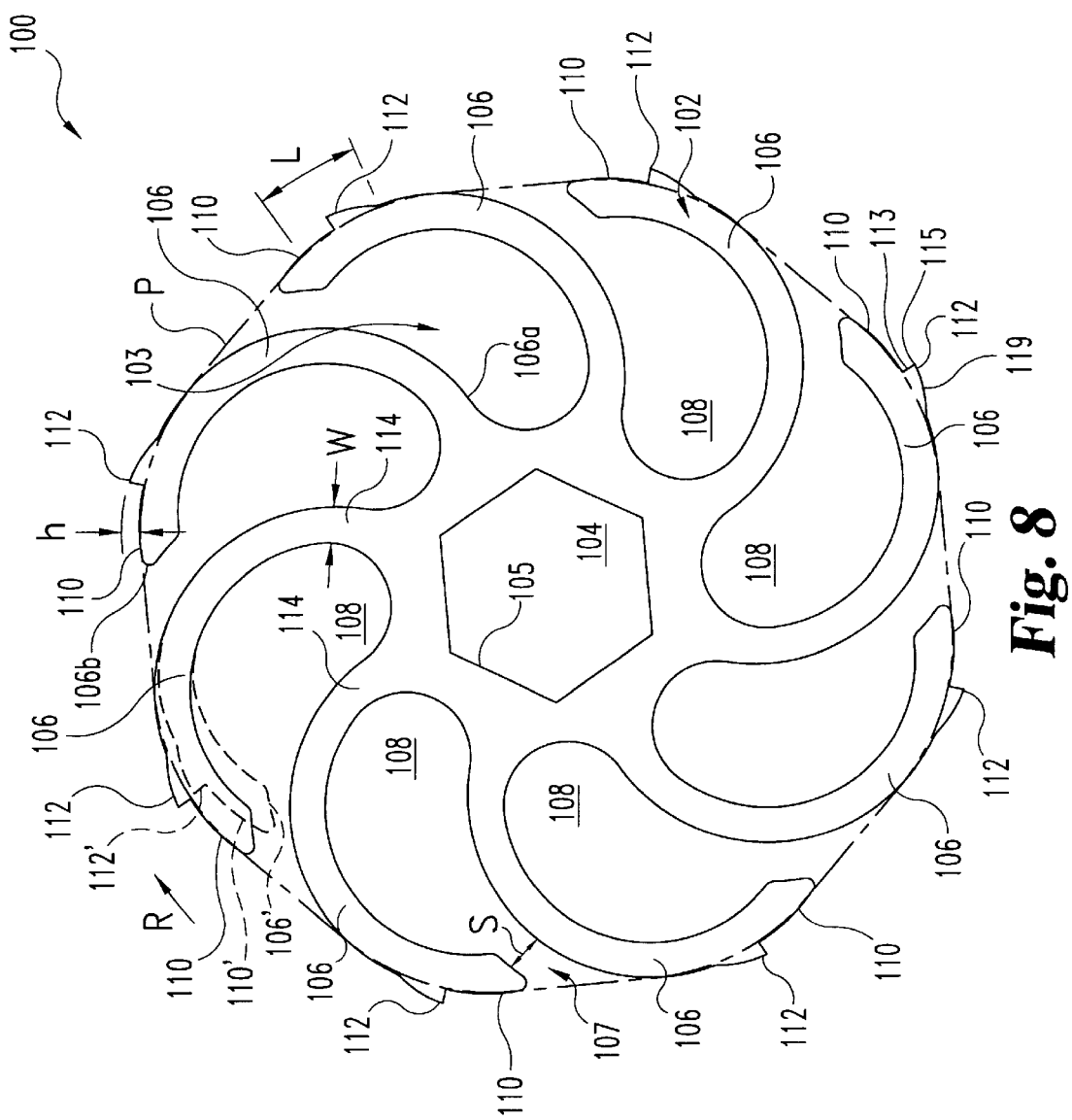

DEVICES FOR SUPPORTING BONY STRUCTURES

BACKGROUND OF THE INVENTION

The present invention concerns a device for supporting bony structures. In particular, the present invention device is directed to an end cap for use with a device for supporting bony structures.

The repair and reconstruction of bony structures is sometimes accomplished by directly fixing adjacent bony structures to each other, such as by a plate. In other instances, bone growth inducing material can be introduced between the adjacent bony structures, which over time results in a solid bony connection. In some instances, the adjacent bony structures are not sufficiently strong to maintain their patency as the bone heals or the bone grows between the adjacent structures through the bone growth inducing material. In these instances, mesh structures or cages have been provided to engage the adjacent bony structures to provide additional stability. The cages are generally hollow and can be configured to contact the harder cortical bone of the adjacent bony structures. The hollow portion of the cages can be filled with bone growth inducing material. One problem, among others, with cages and other devices inserted between adjacent bony structures is that the device can subside into the adjacent bony structure.

SUMMARY OF THE INVENTION

In one aspect of the invention, a device for supporting weak bony structures is provided. The device includes a body having a first end and a second end for contacting a bony structure. The body has a wall that defines a hollow chamber. An end cap is provided with opposite upper and lower surfaces, and includes a plurality of arms extending from a central ring. Each of the arms having a first end connected with the ring and an opposite second end including an outer surface. Each of the outer surfaces are positionable adjacent the inner surface of the wall of the body when the end cap is inserted into the hollow chamber. Each arm can also include a projection that extends at least partially into one of the wall openings.

In one form, bone growth inducing material in placed into the hollow chamber and a second end cap secured to the other end of the body.

According to another aspect of the invention, a device for supporting weak bony structures is provided. The device includes a body having a first end and a second end for contacting a bony structure and a wall extending therebetween. The inner surface of the wall defines a hollow chamber. An end cap is placed in the hollow chamber adjacent one end of the body. The end cap has a central ring and a plurality of curved arms extending from the ring to contact the body and secure the end cap in the hollow chamber.

In one form, the arms have a first end connected with the ring and an opposite second end having an outer surface for contacting the body. In another form, the outer surfaces of the biased arms form a perimeter extending around an inner portion of the end cap and the second end of each arm is deformable towards the inner portion. In another form, the second end of each arm includes a projection that is received in opening formed in the wall of the body.

According to another aspect of the invention, a device for supporting weak bony structures is provided. The device includes a body having a first end and a second end for contacting a bony structure. The body has a wall with an inner surface extending around a hollow chamber. An end cap is placed in the hollow chamber adjacent one of the ends of the body. The end cap has a plate member with opposite upper and lower surfaces defining parallel planes. The end cap has a plurality of arms deformable generally within these planes from a pre-insertion configuration to a reduced size configuration for insertion of the end cap into the hollow chamber. The plurality of arms are biased from their reduced size configuration to their pre-insertion configuration to contact the wall and maintain the end cap in the hollow chamber.

It is one object of the present invention to provide a device for supporting weak bony structures that includes a chamber for receiving osteogenetic material. A further object resides in features of the device that provide a strong structure that can readily engage adjacent bony structures. Another object is to provide a device for supporting weak bony structures that resists subsidence of the device into the adjacent bony structure.

Other objects, features, aspects, embodiments and particular advantages of the present invention can be discerned from the following written description and accompanying figures.

DESCRIPTION OF THE FIGURES

FIG. 1 is a side elevational view of a device for supporting weak bony structures in accordance with aspect of the present invention.

FIG. 2 is a side elevational view of a further embodiment of a device for supporting weak bony structures.

FIG. 3 is an end elevational view of the device shown in FIG. 2.

FIG. 4 is a top perspective view of the device shown in FIGS. 2 and 3.

FIG. 8 is an enlarged top plan view of an end cap according to another aspect of the present invention.

FIG. 9 is a right side elevational view of the end cap of FIG. 8.

DESCRIPTION OF THE PREFERRED EMBODIMENTS

Figure 5:
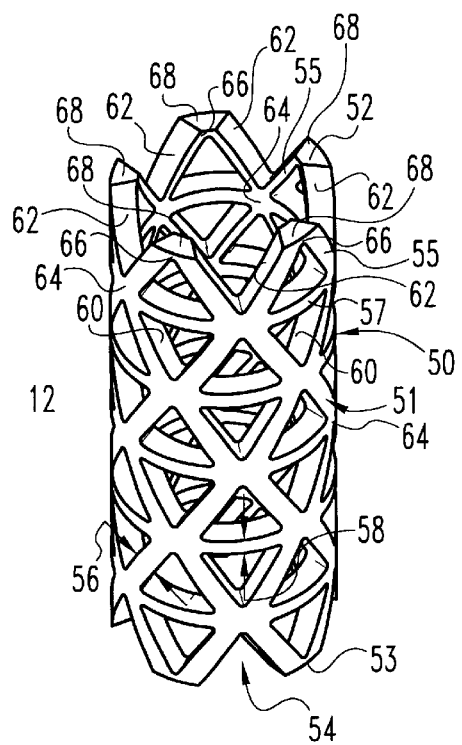
FIG. 5 is a side perspective view of a further embodiment of the device for supporting weak bony structures according to the present invention.

For the purpose of promoting an understanding of the principles of the invention, reference will now be made to preferred embodiments thereof and specific language will be used to describe the same. It will nevertheless be understood that no limitation of the scope of the invention is thereby intended. Any such alterations and further modifications in the invention, and any such further applications of the principles of the invention as described herein are contemplated as would normally occur to one skilled in the art to which the invention relates.

The present invention contemplates a device for supporting weak bony structures. The device is intended for use with current mesh or cage-type devices for engagement with adjacent bony structures, although use with other types of bone supporting devices is also contemplated. The bone supporting device includes a tubular body defining a hollow chamber. The adjacent bony structures can be at least partially received within the hollow chamber, and/or the chamber can be filled with bone growth inducing or osteogenetic material. The ends of the device are provided with flattened end surfaces at the junction between bars defining the tubular body which can be configured to engage the cortical bone of the adjacent bony structures. End caps are provided and placed in the ends of the device to support the adjacent bony structure and reduce subsidence of the device into the adjacent bony structures.

In FIGS. 1–4, a device 10, 10' includes an elongated tubular body 11 formed along a longitudinal axis 14 having a first end 12 and an opposite second end 13. The devices 10, 10' have an inner surface that defines a hollow chamber 16, as shown in FIGS. 3 and 4. The devices also define, in the illustrated embodiments, a substantially cylindrical outer surface 18. It is further contemplated that an end cap, such as end cap 100 discussed further below, may be placed in hollow chamber 16 adjacent first end 12 and a second end cap placed adjacent end 13.

The tubular body 11 is formed by a first group of bars 20 and a second group of bars 25. The first group of bars are oriented at non-perpendicular or non-parallel angles relative to a longitudinal axis 14 of body 11. For clarity, the members of this first group of bars will be identified as angled bars 20. The second group of bars are aligned with their axes substantially perpendicular to the longitudinal axis 14 of the tubular body. The outer surfaces of the bars 20, 25 define the cylindrical outer surface 18 and the inner surfaces of bars 20, 25 define the inner surface 19.

The groups of bars are connected to each other at a plurality of interior joints 30. In accordance with one aspect of the invention, two perpendicular bars 25 and four angled bars 20 converge at a single joint 30. It has been found that this arrangement of angled bars 20 and perpendicular bars 25, as well as the configuration of the interior joints 30, provides the device 10 with substantial axial, torsional and bending strength.

The tubular body includes end joints 32 formed by the intersection or union of a pair of angled bars 20. As can be seen from FIG. 1, the first end 12 and second end 13 of the tubular body 11 do not terminate with a number of perpendicular bars 25, but instead terminate only with the end joints 32 formed by the intersection of angled bars 20.

With the illustrated arrangement of angled bars 20 and perpendicular bars 25, the tubular body 11 defines a plurality of triangular openings 35. Each triangular opening is defined by two angled bars 20 and one perpendicular bar 25. A plurality of triangular openings 35 can be divided into two sets of openings 36, 37. In the first set 36, pairs of oppositely directed triangular openings 35 are spaced axially along the length of the tubular body 11. In the second set 37, similar pairs of oppositely directed triangular openings are axially offset from the pairs of openings in the first set 36, relative to the longitudinal axis 14 of the body 11. Put in other terms, the triangular openings are defined by the bars 20, 25 in pairs of oppositely facing triangles, with successive pairs of openings being staggered circumferentially around the body 11 and along the length of the body. The oppositely directed triangles share a common perpendicular bar defining the base of the triangle. As with the definition of the interior joints 30, it has been found that the pattern of triangular openings 35 enhances the overall stiffness and strength of the devices 10, 10'.

Body 11 further defines end triangular openings 40 that are open at the opposite ends 12 and 13. In particular, the end triangular openings 40 are defined by a pair of angled bars 20 emanating from a vertex 41 at an interior joint 30, as shown in FIG. 2.

A substantially flat end surface 45 is defined at the end joints 32. The end surface 45 defines a surface area that is greater than the cross-sectional area of the angled bars 20 joined at the end joints 32. For example, in one embodiment, the angled bars 20 have a width 21, while the perpendicular bars 25 have a smaller width 26. The angled bars have a cross-sectional area that is the square of the width 26 of the bars 20. The end surface, then, has a surface area that is greater than the combined cross-sectional area of two angled bars 20, or in other words greater than four times the width 21. This enlarged end surface 45 at each of the end joints 32 provides a broader area of contact between the first and second ends 12, 13 of the devices 10, 10' and the adjacent bony structures. In some embodiments, the devices 10, 10' may be disposed co-linearly between adjacent bony structures so that the ends would be in direct contact with the cortical ring of the bony structures. In this instance, the greater surface area of the flat end surfaces 45 will dissipate the load pressure passing from each of the end joints 32 to the adjacent bony structures.

The end joints 32 define an undercut 47 beneath the end surface 45, as shown in FIG. 2. This undercut 47 is preferably in the form of a radius from the end surface to the angled bars 20 intersecting at the end joints 32. The undercuts 47 of each of the end joints 32 can provide an edge for engaging the outer surface of adjacent bony structures to prevent migration of the devices 10, 10' relative to the bony structures.

The embodiment of the device 10 shown in FIG. 1 includes eight rows of perpendicular bars 25 and eight rows of pairs of triangular openings. In this embodiment, the tubular body 11 can have an outer diameter of about 10 mm, an inner diameter of the hollow chamber 16 of about 6.5 mm, and an overall length of about 50 mm. Of course, the diameters and length can be adjusted depending upon the dimensions of the triangular openings. In this specific embodiment, the triangular openings have a height of about 4 mm, and form an equilateral triangle. The pairs of triangular openings are situated at 45 degree intervals around the circumference of the tubular body 11. Furthermore, the angled bars 20 are arranged to subtend approximately a 60 degree angle. In a specific embodiment, the width 21 of the angled bars 20 is about 1.14 mm, while the width 25 of the perpendicular bars 25 is slightly less at about 1.0 mm.

In a second embodiment, the device 10', as shown in FIGS. 2–4, includes only one row of perpendicular bars 25 and one row of pairs of triangular openings 35. In a specific embodiment, the device 10' can have an overall length of about 10 mm with similar outer and inner diameters to the device 10 of FIG. 1.

In the embodiments shown in FIGS. 1–4, the devices 10, 10' include four discrete end surfaces 45, each separated by 90 degrees. In the embodiment of FIG. 1, the device 10 includes eight rows of triangular openings evenly distributed around the circumference of the tubular body 11. In the embodiment of FIG. 2, the device 10' includes only four such triangular openings 35 with four end triangular openings being interspersed at the first and second ends 12, 13 of the body 11.

In an alternative embodiment, a device 50 shown in FIG. 5 includes a tubular body 51 having a first end 52 and a second end 53. The body 11 is defined by a plurality of angled bar 55 and perpendicular bars 57 that are substantially similar to the like-named components of the devices 10, 10'. Similarly, the tubular body 51 defines a plurality of interior triangular openings 60 and triangular end opening 62, as well as interior joints 64 and end joints 66.

The device 50 further includes end surfaces 68 that are similar in configuration to the end surfaces 45 of the previous embodiments. However, unlike the devices 10, 10', the device 50 of FIG. 5 includes five such end surfaces 68 evenly circumferentially distributed around the first end 52 and second end 53. Correspondingly, the device 50 includes 10 rows of interior triangular openings 60 and five end triangular openings 62 at each end 52, 53 of the device 50. The triangular openings 60 still retain the equilateral triangle configuration found in the devices 10, 10'.

In a specific embodiment of the device 50, the angled bars 55 have a width 56 of about 1.3 mm, which is less than the width of the angled bars 20 of the previous embodiment. The perpendicular bars 57 have a width 58 that is about 1 mm, which is the same as the width of the perpendicular bars 25 of the devices 10, 10'. Because additional end surfaces 68 are provided, the device 50 preferably has an outer diameter that is greater than the outer diameter of the devices 10, 10' that have only four such end surfaces. In a specific embodiment, the device 50 can have an outer diameter of about 13 mm and an inner diameter for the hollow chamber 54 of about 10 mm. As with the devices 10, 10', the end surfaces 68 have surface areas that are greater than the combined cross-sectional area of the angled bars 55 intersecting at the end joints 66. Also, like the prior embodiment, the end surfaces 68 preferably have an undercut, similar to the undercut 47 shown in FIG. 2.

Figure 6:
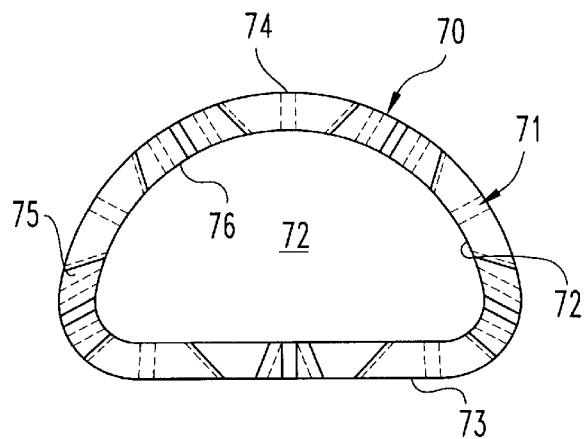
FIG. 6 is a top plan view of yet another embodiment of the present invention showing a non-circular profile.

The embodiments of the device for supporting weak bony structures as shown in FIGS. 1–5 are cylindrical in configuration, having circular cross-sections that are substantially constant throughout the length of the devices. In another embodiment, the external configuration of the device can be modified according to the bony structures for which the device is intended. For example, in FIG. 6, a device 70 is shown formed by a tubular body 71 having an inner surface 76 defining a hollow chamber 72. Unlike the previous cylindrical or circular embodiments, the device 70 has a non-circular cross-section or end view. In this embodiment, the device 70 includes outer surface 73 and a partially elliptical or ovate outer surface 74. In the illustrated embodiment, the device 70 includes five end surfaces uniformly distributed around the perimeter of the tubular body 71. It is understood, however, that more or fewer such end surfaces could be provided.

Figure 7:
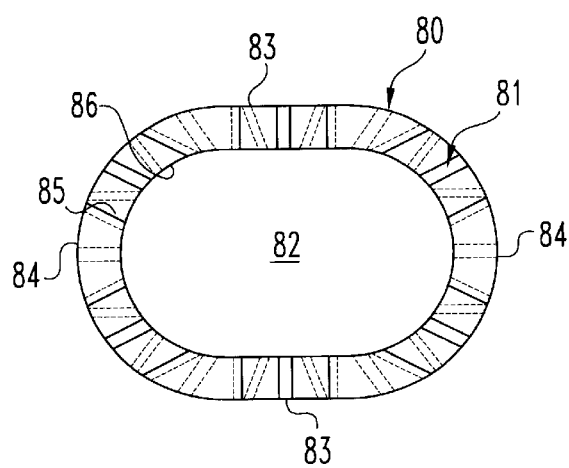
FIG. 7 is an end elevational view of another embodiment of the invention showing a non-circular profile.

In a further alternative embodiment, a device 80 shown in FIG. 7 includes a tubular body 81 having inner surface 86 defining a hollow chamber 82. Again, the device 80 has a non-circular cross-section or configuration along its length. In this embodiment, the tubular body 81 includes opposite flat outer surfaces 83 and opposite curved outer surfaces 84. In the specific embodiment, the curved outer surfaces are partially circular. In the specific embodiment of device 80, the tubular body 81 includes six end surfaces 85 uniformly distributed around the circumference or perimeter of the body. As with the previous embodiments, more or fewer such end surfaces can be provided. Likewise, the device 80, as well as the device 70, can be provided in various lengths, depending upon the adjacent bony structure.

In accordance with the present invention, end cap 100 of FIG. 8 is provided for use with a device that supports adjacent bony structures. It is contemplated that end cap 100 can be dimensioned and shaped for use with any of the devices 10, 10', 50, 70, and 80. For example, in the illustrated embodiments discussed below, and as shown in FIG. 1, a first end cap 100 is placed in hollow chamber 16 of device 10 adjacent first end 12, and a second end cap 100 is placed in hollow chamber 16 adjacent second end 13. However, it should be understood that end cap 100 has application with other types of bone supporting devices as would be understood by those skilled in the art, and that reference hereinbelow to a specific one of the devices 10, 10' etc. is provided for clarity in illustrating the present invention and should not be construed as limiting the present invention to application with illustrated devices.

Referring now to FIG. 8, end cap 100 includes a plate member 102 that defines a plurality of openings therethrough. Plate member 102 includes an inner ring 105 that is centered around a tool opening 104. Tool opening 104 as illustrated as a hexagonal shape, but can also be a slotted opening, threaded opening, or other shaped opening configured to engage a driving tool.

Extending radially outwardly from ring 105 are a plurality of arms 106. In the illustrated embodiment, there are eight arms 106; however, more or fewer arms 106 are also contemplated. Each arm 106 has a first end 106a connected with ring 105 and an opposite second end 106b. Preferably, arms 106 are curved between ends 106a and 106b have a pre-insertion configuration as shown in solid lines in FIG. 8. Arms 106 each include an outer surface 110 adjacent second end 106b. Outer surface 110 of each arm 106 has a length L along or adjacent to a perimeter P. Perimeter P extends around end cap 100 and defines an inner portion 103 that includes substantially all of end cap 100, except projections 112. Perimeter P preferably has a shape that corresponds to the inner surface of a device in which cap 100 is to be inserted, such as inner surface 19 of device 10 or 10' (FIG. 3.)

Each arm 106 includes a projection 112 extending from outer surface 110 outside perimeter P. Projections 112 are spaced about perimeter P so that at least one and preferably all of the projections 112 are alignable with, for example, a corresponding opening 35 of device 10. Projections 112 preferably have an endwall 113 extending transversely with respect to perimeter P from outer surface 110 to an outer edge 115. A smooth transition wall 119 is provided from edge 115 to blend into the convex surface of arm 106. Projections 112 are sized to be at least partially received into an opening 35. When one of the projections 112 is positioned in an opening 35 of device 10, end wall 113 contacts one of the bars defining the opening 35 to prevent rotation in the direction opposite arrow R. Transition surface 119 rides along the bars defining the opening to allow rotation in the direction of arrow R. Other embodiments contemplate that projection 112 can be in the form of a raised surface that smoothly transitions between the outer surface of arm 106 and outer surface 110.

End cap 100 has a passageway 107 forming spacing S between adjacent arms 106. Passageway 107 extends from second end 106b to a relieved portion 108 adjacent first end 106a. Relieved portions 108 provide arms 106 with a reduced thickness having a width W, reducing the stiffness of arm 106 and facilitating deformation of arm 106 from its pre-insertion configuration. It is contemplated that each arm 106 has a constant width W along the length of arm 106 between first end 106a and second end 106b. It is further contemplated that spacing S can be variable between adjacent arms 106, and that width W can be variable along the length of arms 106 such that, for example, arms 106 have an increasing width from first end 106a to second end 106b. Passageway 107 and relieved portions 108 also provide openings through end cap 100 to facilitate bone growth through the device and fusion between the adjacent bony structures.

As shown in FIG. 9, a side elevational view of end cap 100, plate member 102 has a substantially constant thickness t between an upper surface 116 and a lower surface 117. Surfaces 116, 117 define parallel planes that include end cap 100. Surfaces 116, 117 are oriented in a hollow chamber of a device supporting adjacent bony structures such that surfaces 116, 117 extend generally parallel to the bony structures.

Arms 106 are deformable towards inner portion 103 as indicated by the position of arm 106' illustrated in a phantom line in FIG. 8 so that end cap 100 assumes a reduced size configuration for insertion into hollow chamber 16. The deformation of arms 106 is confined substantially between the parallel planes defined by upper surface 116 and lower surface 117. A tool (not shown) is placed in tool opening 104 and end cap 106 is placed adjacent first end 12. End cap 100 is rotated in the direction indicated by arrow R, bringing outer surface 110 into contact with inner surface 19 of device 10 and deforming arms 106 and outer surface 110 from their pre-insertion configuration to a reduced size configuration. Arms 106 are moved towards inner portion 103 as indicated by arm 106' in the reduced size configuration. Passageways 107 provide clearance between adjacent arms 106 to facilitate deformation. For purposes of clarity, only one arm 106 is shown in a deformed condition in FIG. 9. However, it should be understood that each of the arms 106 or a portion of arms 106 can be deformed during insertion. This deformation reduces the spacing S between adjacent arms 106, and the overall deformation is limited by the size of spacing S between adjacent arms 106.

Outer surface 110 contacts inner surface 19 and holds end cap 100 in hollow chamber 16. It should be understood that outer surface 110 may have a point contact with inner surface 19 or may be in contact with inner surface 19 along all or a portion of the length of outer surface 110. In another embodiment, the inner surface 19 of hollow chamber 16 can be flared towards outer surface 18 at the end of device 10 to facilitate end cap 100 insertion. Rotation of end cap 100 in the direction opposite arrow R is resisted by the curvature of arms 106, preventing backout of end cap 100 from chamber 16.

In the illustrated embodiment, it is contemplated that arms 106 are biased to return to their pre-insertion configuration when a deformation force is removed from the arms. This allows arms 106 to form a perimeter P that is substantially conformable to inner surface 19 of device 10. Each arm 106 is deformed towards inner portion 103 as projection 112 of outer surface 110 rides along inner surface 19. When end cap 100 is rotated to the desired depth into hollow chamber 16, at least one biased arm 106 forces its projection 112 at least partially into an adjacent opening 35. The outer surface 110 contacts the device 10, supporting and maintaining end cap 100 in hollow chamber 16. It is contemplated that outer surface 110 may contact inner surface 19 at a point or along all or a portion of length L. Alternatively, outer surface 110 may not contact inner surface 19 at all, and only projection 112 contacts device 10 in opening 35.

Each of the devices 10, 10', 50, 70, 80, and 100 shown in the Figures is preferably fabricated from a biocompatible material. The material is also preferably strong enough to withstand the application of external compressive, axial, torsional and bending loads, as well as being strong enough to provide support for the adjacent weak bony structures. End caps 100 and 120 must also have the necessary strength to support the adjacent bony structures and allow the end caps to be deformed yet retain their pre-insertion bias. In one embodiment, the devices are formed entirely of titanium. Other biocompatible metals can be used such as surgical grade stainless steel. While the devices of the preferred embodiments are formed of a solid metallic material, the present invention also contemplates forming the devices of a porous, yet strong, material. For example, the devices could be formed from a porous tantalum material, such as the material HEDROCEL® provided by Implex Corporation.

In use, each of the devices 10, 10', 50, 70, 80 can be engaged around the ends of adjacent bony structures. The devices can be used to hold the adjacent bony structures in immediate contact. Alternatively, the devices can hold the bony structures apart so that a gap is formed between the structures. In these instances, the hollow chambers of each of the devices can be filled with bone growth inducing or osteogenetic material. In these embodiments, end cap 100 is placed into one end of the device. The bone growth inducing or ostegenic material is then placed into the hollow interior of the device. A second end cap 100 may then be placed in the opposite end of the device. Alternatively, the end caps may both be placed in the ends of the device after filling the hollow chamber with bone growth inducing or osteogenic material.

Any suitable osteogenetic material or composition is contemplated, including autograft, allograft, xenograft, demineralized bone, synthetic and natural bone graft substitutes, such as bioceramics and polymers, and osteoinductive factors. Where bony material is placed within the chambers, the material can be re-packed into the hollow chamber of the device, or can even be pushed through the plurality of triangular openings 35 once the device is in position. In some cases, the bone growth inducing materials require a separate carrier to hold the materials within the gap between the adjacent bony structures. These carries can include collagen-based carriers, or even bioceramic materials, such as BIOGLASS®, hydroxyapetite and calcium phosphate compositions. Moreover, some of the osteogenetic compositions contained within the devices of the present invention can comprise a therapeutically effective amount of a bone morphogenetic protein held within a suitable carrier material. The carrier material can be provided in the form of a sponge, a block, or even a folded sheet.

In an alternative use of the devices of the present invention, the devices can be directly and entirely situated in the gap between adjacent bony structures. In this instance, the end surfaces, such as end surface 45 of device 10', will directly contact the bone. Most preferably, the end surfaces will only contact the hard cortical bone at the outer perimeter of the bony structure. When used in this manner, the hollow chamber of the devices are most preferably packed with an osteogenetic or bone growth material and end cap 100 is placed in the ends of the devices, as described above. The end caps 100 help retain the material in the hollow chamber of the device. End caps 100 also provide a greater load bearing area for the adjacent bony structures, which is useful in preventing subsidence of the device into the adjacent bony structures.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. For example, the devices 10, 10', 50, 70 and 80 can be cut to various lengths to accommodate variations in the anatomy of the bony structures.

What is claimed is:

1. A device for supporting weak bony structures, comprising:
   a body having a first end and a second end for contacting a bony structure, said body having a wall extending therearound and a hollow chamber having a perimeter defined by an inner surface of said wall; and
   an end cap positionable in said hollow chamber adjacent one of said ends of said body, said end cap having opposite upper and lower surfaces, said end cap including:
   a central ring;
   a plurality of arms extending radially from said central ring, each of said arms having a first end connected with said ring and an opposite second end including an outer surface, each of said outer surfaces positioned adjacent said perimeter when said end cap is inserted into said hollow chamber.

2. The device according to claim 1, wherein said end cap is deformable from a pre-insertion configuration to a reduced size configuration for insertion of said end cap in said hollow chamber, said end cap being biased towards said pre-insertion configuration so at least one of said outer surfaces contacts said wall after insertion in said hollow chamber.

3. The device according to claim 1, wherein said end cap is positionable in said hollow chamber by rotating said end cap in a first direction with respect to said body.

4. The device according to claim 1, wherein said outer surfaces extend between said upper and lower surfaces of said end cap.

5. The device according to claim 1, wherein each of said arms is curved and includes a relieved portion adjacent said first end.

6. The device according to claim 1, wherein a passageway is defined between adjacent ones of said plurality of arms.

7. The device according to claim 1, wherein said wall of said body has a plurality of openings therethrough communicating with said hollow chamber and each of said outer surfaces includes a projection positionable at least partially into a corresponding one of said openings.

8. The device according to claim 7, wherein each of said plurality of openings has a triangular shape.

9. The device according to claim 8, wherein said triangular-shaped openings define equilateral triangles.

10. The device according to claim 1, wherein said central ring of said end cap includes a tool opening.

11. The device according to claim 1, further comprising bone growth inducing material in said chamber.

12. The device according to claim 11, further comprising a second end cap identical to said end cap positionable in the other end of said body.

13. The device according to claim 1, wherein said upper and lower surfaces extend generally parallel to the adjacent bony structures.

14. A device for supporting weak bony structures, comprising:
   a body having a first end and a second end for contacting a bony structure, said body having a wall extending therearound and a hollow chamber defined by an inner surface of said wall, said inner surface defining a perimeter therearound; and
   an end cap positionable in said hollow chamber adjacent one of said ends of said body, said end cap having a central ring and a plurality of curved arms extending radially from said ring, at least one of said plurality of arms contactable with said body to maintain said end cap in said hollow chamber.

15. The device according to claim 14, wherein each of said plurality of arms has a first end connected with said ring and an opposite second end having an outer surface.

16. The device according to claim 15, wherein said arms are biased so that said outer surfaces contact said inner surface of said wall.

17. The device according to claim 16, wherein said arms are deformable to a reduced size configuration for positioning said end cap in said hollow chamber.

18. The device according to claim 15, wherein each of said arms includes a relieved portion adjacent said first end.

19. The device according to claim 14, wherein a passageway is defined between adjacent ones of said plurality of arms.

20. The device according to claim 14, wherein said wall of said body has a plurality of openings therethrough communicating with said hollow chamber, and each of said arms includes an outer surface and a projection extending from said outer surface at least partially into a corresponding one of said openings when said end cap is positioned in said hollow chamber.

21. The device according to claim 20, wherein said end cap is positionable in said hollow chamber by rotating said end cap in a first direction with respect to said body.

22. The device according to claim 21, wherein said projection includes an end wall extending from said outer surface to an outer edge, said end wall contactable with said wall of said device when said projection is in one of said openings to prevent rotation of said end cap in a second direction opposite said first direction.

23. The device according to claim 14, wherein said end cap is in the form of a plate member having a substantially constant thickness between an upper surface and a lower surface of said end cap.

24. The device according to claim 14, wherein said perimeter is substantially circular.

25. A device for supporting weak bony structures, comprising:
   a body having a first end and a second end for contacting a bony structure, said body having a wall extending therearound and a hollow chamber defined by an inner surface of said wall; and
   an end cap for placement in said hollow chamber adjacent one of said ends of said body, said end cap having opposite upper and lower surfaces and at least one opening therebetween to permit bone growth therethrough, said upper and lower surfaces defining parallel planes and said end cap having a plurality of arms deformable generally within said planes from a pre-insertion configuration to a reduced size configuration for insertion of said end cap into said hollow chamber, said plurality of arms biased from said reduced size configuration to said pre-insertion configuration to contact said wall to maintain said end cap in said hollow chamber.

26. The device according to claim 25, wherein:
   said wall of said body has a plurality of openings therethrough communicating with said hollow chamber; and each of said plurality of arms includes an outer surface extending between said upper and lower surfaces, each of said plurality of arms further including a projection extending from said outer surface and positionable in one of said openings.

27. The device according to claim 26, wherein said end cap is positionable in said hollow chamber by rotating said end cap in a first direction with respect to said body.

28. The device according to claim 27, wherein said projection includes an end wall extending from said outer surface to an outer edge, said end wall contactable with said wall of said device when said projection is in one of said openings to prevent rotation of said end cap in a second direction opposite said first direction.

29. The device according to claim 25, wherein said end cap includes a central ring defining a tool opening.

30. The device according to claim 25, further comprising bone growth inducing material in said chamber.

31. The device according to claim 30, further comprising a second end cap positionable in the other end of said body identical to said end cap.

32. The device according to claim 25, wherein said end cap has a substantially constant thickness between said upper and lower surfaces.

33. The device according to claim 25, wherein said end cap includes a central ring and said plurality of arms extend radially from said ring.

34. The device according to claim 33, wherein each of said arms is curved.

35. The device according to claim 34, wherein each of said arms has a constant width along said arm.

36. The device according to claim 34, wherein a passageway is defined between adjacent ones of said plurality of arms.

37. A device for supporting weak bony structures, comprising:
   a body having a first end and a second end for contacting a bony structure, said body having a wall extending therearound and a hollow chamber having a perimeter defined by an inner surface of said wall; and
   an end cap positionable in said hollow chamber adjacent one of said ends of said body, said end cap having opposite upper and lower surfaces, said end cap including:
   a central ring;
   a plurality of arms extending from said central ring, each of said arms having a first end connected with said ring and an opposite second end including an outer surface, each of said outer surfaces positioned adjacent said perimeter when said end cap is inserted into said hollow chamber, wherein said outer surfaces extend between said upper and lower surfaces of said end cap.

38. The device according to claim 37, wherein said end cap is deformable from a pre-insertion configuration to a reduced size configuration for insertion of said end cap in said hollow chamber, said end cap being biased towards said pre-insertion configuration so at least one of said outer surfaces contacts said wall after insertion in said hollow chamber.

39. The device according to claim 37, wherein said end cap is positionable in said hollow chamber by rotating said end cap in a first direction with respect to said body.

40. The device according to claim 37, wherein each of said arms is curved and includes a relieved portion adjacent said first end.

41. The device according to claim 37, wherein a passageway is defined between adjacent ones of said plurality of arms.

42. The device according to claim 37, wherein said wall of said body has a plurality of openings therethrough communicating with said hollow chamber and each of said outer surfaces includes a projection positionable at least partially into a corresponding one of said openings.

43. The device according to claim 37, wherein said central ring of said end cap includes a tool opening.

44. The device according to claim 37, further comprising bone growth inducing material in said chamber.

45. The device according to claim 37, wherein said upper and lower surfaces extend generally parallel to the adjacent bony structures.

46. The device according to claim 37, wherein said arms extend radially from said central ring.

47. A device for supporting weak bony structures, comprising:
   a body having a first end and a second end for contacting a bony structure, said body having a wall extending therearound and a hollow chamber having a perimeter defined by an inner surface of said wall; and
   an end cap positionable in said hollow chamber adjacent one of said ends of said body, said end cap having opposite upper and lower surfaces, said end cap including:
   a central ring;
   a plurality of arms extending from said central ring, wherein each of said arms having a first end connected with said ring and an opposite second end including an outer surface, each of said arms being curved and including a relieved portion adjacent said first end, each of said outer surfaces positioned adjacent said perimeter when said end cap is inserted into said hollow chamber.

48. The device according to claim 47, wherein said end cap is deformable from a pre-insertion configuration to a reduced size configuration for insertion of said end cap in said hollow chamber, said end cap being biased towards said pre-insertion configuration so at least one of said outer surfaces contacts said wall after insertion in said hollow chamber.

49. The device according to claim 47, wherein said end cap is positionable in said hollow chamber by rotating said end cap in a first direction with respect to said body.

50. The device according to claim 47, wherein said outer surfaces extend between said upper and lower surfaces of said end cap.

51. The device according to claim 47, wherein a passageway is defined between adjacent ones of said plurality of arms.

52. The device according to claim 47, wherein said wall of said body has a plurality of openings therethrough communicating with said hollow chamber and each of said outer surfaces includes a projection positionable at least partially into a corresponding one of said openings.

53. The device according to claim 47, wherein said central ring of said end cap includes a tool opening.

54. The device according to claim 47, further comprising bone growth inducing material in said chamber.

55. The device according to claim 47, wherein said upper and lower surfaces extend generally parallel to the adjacent bony structures.

56. A device for supporting weak bony structures, comprising:
   a body having a first end and a second end for contacting a bony structure, said body having a wall extending therearound and a hollow chamber defined by an inner surface of said wall; and an end cap for placement in said hollow chamber adjacent one of said ends of said body, said end cap having opposite upper and lower surfaces, said upper and lower surfaces defining parallel planes and said end cap having a plurality of arms deformable generally within said planes from a pre-insertion configuration to a reduced size configuration for insertion of said end cap into said hollow chamber, said plurality of arms biased from said reduced size configuration to said pre-insertion configuration to contact said wall to maintain said end cap in said hollow chamber, wherein said end cap includes a central ring defining a tool opening.

57. The device according to claim 56, wherein:

said wall of said body has a plurality of openings therethrough communicating with said hollow chamber; and each of said plurality of arms includes an outer surface extending between said upper and lower surfaces, each of said plurality of arms further including a projection extending from said outer surface and positionable in one of said openings.

58. The device according to claim 57, wherein said end cap is positionable in said hollow chamber by rotating said end cap in a first direction with respect to said body.

59. The device according to claim 58, wherein said projection includes an end wall extending from said outer surface to an outer edge, said end wall contactable with said wall of said device when said projection is in one of said openings to prevent rotation of said end cap in a second direction opposite said first direction.

60. The device according to claim 56, further comprising bone growth inducing material in said chamber.

61. The device according to claim 56, wherein said end cap has a substantially constant thickness between said upper and lower surfaces.

62. The device according to claim 56, wherein said plurality of arms extend radially from said ring.

63. The device according to claim 62, wherein each of said arms is curved.

64. The device according to claim 63, wherein a passageway is defined between adjacent ones of said plurality of arms.

65. A device for supporting weak bony structures, comprising:

a body having a first end and a second end for contacting a bony structure, said body having a wall extending therearound and a hollow chamber defined by an inner surface of said wall, said chamber adapted to receive bone growth material therein; and an end cap for placement in said hollow chamber adjacent one of said ends of said body, said end cap having opposite upper and lower surfaces, said upper and lower surfaces defining parallel planes and said end cap having a plurality of arms deformable generally within said planes from a pre-insertion configuration to a reduced size configuration for insertion of said end cap into said hollow chamber, said plurality of arms biased from said reduced size configuration to said pre-insertion configuration to contact said wall to maintain said end cap in said hollow chamber.

66. The device according to claim 65, wherein:

said wall of said body has a plurality of openings therethrough communicating with said hollow chamber; and each of said plurality of arms includes an outer surface extending between said upper and lower surfaces, each of said plurality of arms further including a projection extending from said outer surface and positionable in one of said openings.

67. The device according to claim 66, wherein said end cap is positionable in said hollow chamber by rotating said end cap in a first direction with respect to said body.

68. The device according to claim 67, wherein said projection includes an end wall extending from said outer surface to an outer edge, said end wall contactable with said wall of said device when said projection is in one of said openings to prevent rotation of said end cap in a second direction opposite said first direction.

69. The device according to claim 65, wherein said end cap has a substantially constant thickness between said upper and lower surfaces.

70. The device according to claim 65, wherein said end cap includes a central ring and said plurality of arms extend radially from said ring.

71. The device according to claim 70, wherein each of said arms is curved.

72. The device according to claim 71, wherein a passageway is defined between adjacent ones of said plurality of arms.

* * * * *